United States Patent
Kanagala (10) Patent No.: US 9,251,314 B2
(45) Date of Patent: Feb. 2, 2016

(54) METHODS AND SYSTEMS FOR CLOUD BASED USAGE MONITORING AND ADAPTIVE ENFORCEMENT FOR MEDICATIONS

(71) Applicant: Santana Row Venture LLC, San Jose, CA (US)

(72) Inventor: Sameer Kanagala, San Jose, CA (US)

(73) Assignee: Wellocity, Inc., San Jose, CA (US)

(*) Notice: Subject to any disclaimer, the term of this patent is extended or adjusted under 35 U.S.C. 154(b) by 201 days.

(21) Appl. No.: 13/940,227

(22) Filed: Jul. 11, 2013

(65) Prior Publication Data

US 2014/0058560 A1 Feb. 27, 2014

Related U.S. Application Data

(60) Provisional application No. 61/691,517, filed on Aug. 21, 2012, provisional application No. 61/781,006, filed on Mar. 14, 2013.

(51) Int. Cl.
- *G08B 21/00* (2006.01)
- *G06F 19/00* (2011.01)
- *A61J 1/00* (2006.01)

(52) U.S. Cl.
CPC .............. *G06F 19/3462* (2013.01); *A61J 1/00* (2013.01); *G06F 19/34* (2013.01); *G06F 19/3456* (2013.01)

(58) Field of Classification Search
CPC ......... G06F 19/00; G06F 19/30; G06F 19/32; G06F 19/322; G06F 19/34; G06F 19/3406; G06F 19/3456; G06F 19/3462; G06F 19/3487; G06Q 50/22; G06Q 50/24; A61J 1/00; A61J 1/03

See application file for complete search history.

(56) References Cited

U.S. PATENT DOCUMENTS

| 5,710,551 | A | 1/1998 | Ridgeway |
| 5,781,442 | A * | 7/1998 | Engleson et al. ............. 700/214 |
| 6,604,650 | B2 * | 8/2003 | Sagar ................. 221/3 |
| 7,269,476 | B2 * | 9/2007 | Ratnakar ....................... 700/236 |
| 7,366,675 | B1 * | 4/2008 | Walker et al. ..................... 705/2 |
| 7,747,454 | B2 | 6/2010 | Bartfeld et al. |
| 7,945,461 | B2 | 5/2011 | Sekura |
| 7,956,727 | B2 | 6/2011 | Loncar |
| 8,068,015 | B2 * | 11/2011 | Burg ....................... 340/309.16 |
| 8,108,068 | B1 * | 1/2012 | Boucher et al. ............... 700/236 |
| 8,193,918 | B1 | 6/2012 | Shavelsky et al. |
| 8,725,291 | B2 * | 5/2014 | Czaja et al. .................... 700/240 |
| 8,749,379 | B2 * | 6/2014 | Muecke ............ G07C 9/00126 340/5.7 |
| 2003/0086338 | A1 * | 5/2003 | Sastry et al. ..................... 368/10 |
| 2007/0016443 | A1 | 1/2007 | Wachman et al. |
| 2008/0105588 | A1 * | 5/2008 | Tran et al. ..................... 206/534 |

(Continued)

*Primary Examiner* — Steven Lim
*Assistant Examiner* — Ryan Sherwin
(74) *Attorney, Agent, or Firm* — DLA Piper LLP (US)

(57) ABSTRACT

A cloud based system that constantly monitors the consumption of each medication by an individual, specifies medication regimes and schedules and provides a means of enforcing compliance based on both local and cloud based intelligence. Enforcing compliance to a medication schedule is achieved through complex logic that correlates events from the medication bottles; behavior learned from the individual, individual's schedules and geo-location. The system employs this complex logic per medication and generates a variety of email, phone call, SMS, MMS, voice messages, audio, visual and multimedia cues and alerts to enforce compliance. These same alerts are also used by multiple caregivers, who can further reinforce compliance by the patient via similar types of communications.

1 Claim, 10 Drawing Sheets

(56) References Cited

U.S. PATENT DOCUMENTS

| | | | |
|---|---|---|---|
| 2010/0185456 A1* | 7/2010 | Kansal | 705/2 |
| 2010/0328099 A1 | 12/2010 | Wachman et al. | |
| 2012/0003928 A1* | 1/2012 | Geboers et al. | 455/41.1 |
| 2012/0163132 A1 | 6/2012 | Downey et al. | |
| 2013/0110283 A1* | 5/2013 | Baarman et al. | 700/236 |

* cited by examiner

| ID | Name | Nickname | Description | 1st Dosage Time | 2nd Dosage Time | 3rd Dosage Time | 4th Dosage Time | Patient_Email | OBK_ID |
|---|---|---|---|---|---|---|---|---|---|
| 1 | Adanax | Orange | Allergy Relief | 09:00:00 | 13:00:00 | 18:00:00 | 21:00:00 | ac@gmail.com | 58PU128 |
| 2 | Singulair | Yellow | Asthma Relief | 08:00:00 | 20:00:00 | NULL | NULL | ac@gmail.com | 58PU129 |
| 3 | Prevacid | Purple | Antacid | 10:00:00 | NULL | NULL | NULL | ac@gmail.com | 58PU130 |
| 4 | Adanax | Orange | Allergy Relief | 09:00:00 | 13:00:00 | 18:00:00 | 21:00:00 | jb@gmail.com | 58MT128 |
| 5 | Singulair | Yellow | Asthma Relief | 08:00:00 | 20:00:00 | NULL | NULL | jb@gmail.com | 58MT129 |
| 6 | Prevacid | Purple | Antacid | 10:00:00 | NULL | NULL | NULL | jb@gmail.com | 58MT130 |

METHODS AND SYSTEMS FOR CLOUD BASED USAGE MONITORING AND ADAPTIVE ENFORCEMENT FOR MEDICATIONS

PRIORITY CLAIM

This application claims the benefit under 35 USC 119(e) to U.S. Provisional Patent Application Ser. No. 61/781,006, filed on Mar. 14, 2013 and titled "Methods and Systems for Cloud Based Usage Monitoring and Adaptive Enforcement for Medications," and to U.S. Provisional Patent Application Ser. No. 61/691,517, filed on Aug. 21, 2012 and titled "Methods and Systems for Internet Based Usage Monitoring and Enforcement for Medications," both of which are incorporated by reference herein.

TECHNICAL FIELD

A cloud based system that constantly monitors the consumption of each medication by an individual, specifies medication regimens and schedules and provides a means of enforcing compliance based on both local and cloud based intelligence is disclosed.

BACKGROUND OF THE INVENTION

A common problem for medical patients and caregivers is monitoring the usage of medications and enforcing compliance for medications regimen and schedules. Timely consumption of the required dosage and types of medication are of critical importance, as evidenced by the fact that failing to take medications at the proper time in the proper dosage leads to 125,000 deaths per year, according to the World Health Organization. Some of the most critical and seemingly simple questions relating to compliance with medication regimens are: (1) did you take your medications today? (2) at the prescribed time? and (3) the prescribed number of times? The responses to these questions are dependent on age, language barriers, socio-economic status, and conditions such as dementia and depression.

While there are scores of medication reminder software applications (apps) and services available, many of them are just glorified alarm clocks and quickly go from utility to annoying, and with random snoozing and cancellations by patients, these solutions are full of false positives and remind you of the boy who cried wolf.

What is needed is an automated and efficient system and method for monitoring the actual usage of medications and for enforcing compliance with medication regimens and schedules.

SUMMARY OF THE INVENTION

The embodiments are adaptive systems that enforce medication compliance based on both local and cloud based intelligence by constantly monitoring the consumption of each medication by a patient. They also provides a reliable cloud based system for specifying medication regimes and schedules.

Enforcing compliance with a medication schedule is achieved through an adaptive system that correlates events from smart dispensers used to hold medication, behavior learned from the patient, and the patient's schedule and geo-location, for each medication. The embodiments described herein evaluate all of these parameters for each patient and per medication to generate a variety of email, short message service (SMS), multimedia messaging service (MMS), phone calls, voice messages, audio, visual and multimedia cues, and other alerts to constantly adapt the enforcement compliance logic.

The following are some of the benefits the proposed system will provide by ensuring compliance with medication regimens:

(1) Prevent life-threatening missed dosages;
(2) Prevent life-threatening accidental overdoses;
(3) Prevent use of expired medications;
(4) Prevent the consumption of drugs to which the patient is allergic;
(5) Prevent use of contra-indicated medications;
(6) Improve drug metabolism with timely administration;
(7) Ensure continuity in care by streamlining the ordering of refills; and
(8) Ensure safety of both patients and community with timely administration of psychiatric medications.

The use of the cloud provides a reliable system for specifying medication regimes and schedules by the patient or a caregiver and importing data from a pharmacy database or a concierge service.

The use of the cloud also enables multiple caregivers to monitor the medication compliance of the patient from anywhere and at any time and provides an additional level of enforcement via email, phone, SMS, MMS, and social media contact, all of which are above and beyond the direct enforcement mechanisms the proposed system provides to the patient.

Events generated from a smart dispenser definitively show that the patient opened and closed the bottle and thus took the medication at the right dosage, and/or indicates the exact change in weight of the smart dispenser which can be used to determine the number of pills that have been added to or removed from the smart dispenser. This knowledge allows the proposed system to constantly review schedules per medication and resolve all past, current and upcoming alerts based on an event, a patient's learned behavior, and a patient's geo-location.

The embodiments do not require alarms to be generated for each medication, each time. Rather, it uses its built-in intelligence to enforce the requirements of a cloud based medication schedule by using events generated by the medication bottles and the learned behavior and geo-location of the patient. The embodiments then make use of smartphones, tablets and other electronic devices to generate a variety of email, SMS, MMS, phone call, voice message, audio, visual and multimedia cues and other alerts to enforce compliance by the patient carrying the smartphone etc. These same alerts are also used by multiple caregivers who can further reinforce compliance by the patient.

The embodiments remove false positives by providing direct and timely feedback to the patient utilizing events, behavior, and location and feedback mechanisms to enforce compliance locally. They also provide indirect feedback to the individual through caregivers based on the cloud based compliance enforcement mechanism. All medication schedules and enforcement mechanisms are defined in the cloud and all monitoring data is also stored in the cloud allowing tracking, trending, and analytics.

Some conditions that can be monitored using the embodiments include:

(1) Dosage Compliance—how often daily, weekly etc.
(2) Potential overdose
(3) Missed dosage(s)
(4) Time of usage—timely administration improves medication metabolism (5) Getting medications mixed up—overdose on one medication and skipping another
(6) Use of expired medications
(7) Potential medication allergies
(8) Potential use of contraindicated medications
(9) When to order refills
(10) Complete inactivity—Is the patient incapacitated?

Other aspects and advantages of the invention will become apparent from the following detailed description, taken in combination with the accompanying drawings, illustrating by way of example the principles of the invention.

BRIEF DESCRIPTION OF THE DRAWINGS

A more complete understanding of the embodiments may be derived by referring to the detailed description when considered in conjunction with the following figures. wherein like reference numbers refer to similar elements throughout the figures.

DETAILED DESCRIPTION OF THE PREFERRED EMBODIMENTS

Embodiments of the inventions will now be described. For the purpose of this description, the individuals of this system whose compliance is being monitored and affected are referred to as patients. The use of the word "patient" or "patients" is not meant to limit the scope of the invention or to require any kind of doctor/patient relationship or any other kind of medical or legal relationship with the individuals.

As used herein, the term "medication" refers to any kind of medicine, prescription or otherwise. Further, the term "medication" includes medicine in any form, including, without limitation pills, salves, creams, powders, ointments, capsules, injectable medications, drops, vitamins and suppositories. The scope of this invention is not limited by the type, form or dosage of the medication.

As used herein, the term "caregivers" refers to both unskilled individuals such as friends, family members and coworkers and skilled medical professionals such as doctors and nurses. All caregivers are assumed to have varying degrees of skills and motivation to help the patients and are explicitly authorized by the patients to configure and monitor their medication data on the internet based server.

Embodiments of the invention may be described herein in terms of functional and/or logical block components and various processing steps. It should be appreciated that such block components may be realized by any number of hardware, software, and/or firmware components configured to perform the specified functions. For example, an embodiment of the invention may employ various integrated circuit components, e.g., memory elements, digital signal processing elements, logic elements, look-up tables, or the like, which may carry out a variety of functions under the control of one or more microprocessors or other control devices. In addition, those skilled in the art will appreciate that embodiments of the present invention may be practiced in conjunction with any number of data transmission and data formatting protocols and that the system described herein is merely one example embodiment of the invention.

For the sake of brevity, conventional techniques related to signal processing; data transmission; signaling; network control; wireless RF, Bluetooth, ZigBee (and other variants of the IEEE 802.15 protocol), IEEE 802.11 (any variation), and IrDA (infrared); ultrasound interfaces and specifications; and other functional aspects of the systems (and the individual operating components of the systems) may not be described in detail herein as those conventional techniques are known in the art. Furthermore, connecting lines shown in the figures contained herein are intended to represent example functional relationships and/or physical couplings between the various elements. It should be noted that many alternative or additional functional relationships or physical connections may be present in an embodiment of the invention.

The following description refers to elements or nodes or features being "connected" or "coupled" together. As used herein, unless expressly stated otherwise, "connected" means that one element/node/feature is directly joined to (or directly communicates with) another element/node/feature, and not necessarily mechanically. Likewise, unless expressly stated otherwise, "coupled" means that one element/node/feature is directly or indirectly joined to (or directly or indirectly communicates with) another element/node/feature, and not necessarily mechanically. The term "exemplary" is used in the sense of "example," rather than "model." Although the figures may depict example arrangements of elements, additional intervening elements, devices, features, or components may be present in an embodiment of the invention.

The present invention relates to a cloud based system that constantly monitors the consumption of each medication by an individual, specifies medication regimes and schedules and provides a means of enforcing compliance based on both local and cloud based intelligence. Enforcing compliance to a medication schedule is achieved through complex logic that correlates events from the medication containers; behavior learned from the patient, patient's schedules and geo-location. In this regard, the following detailed description is merely illustrative in nature and is not intended to limit the embodiments of the invention or the application and uses of such embodiments. Furthermore, there is no intention to be bound by any expressed or implied theory presented in the preceding background, operation, summary or the following detailed description.

Figure 1:
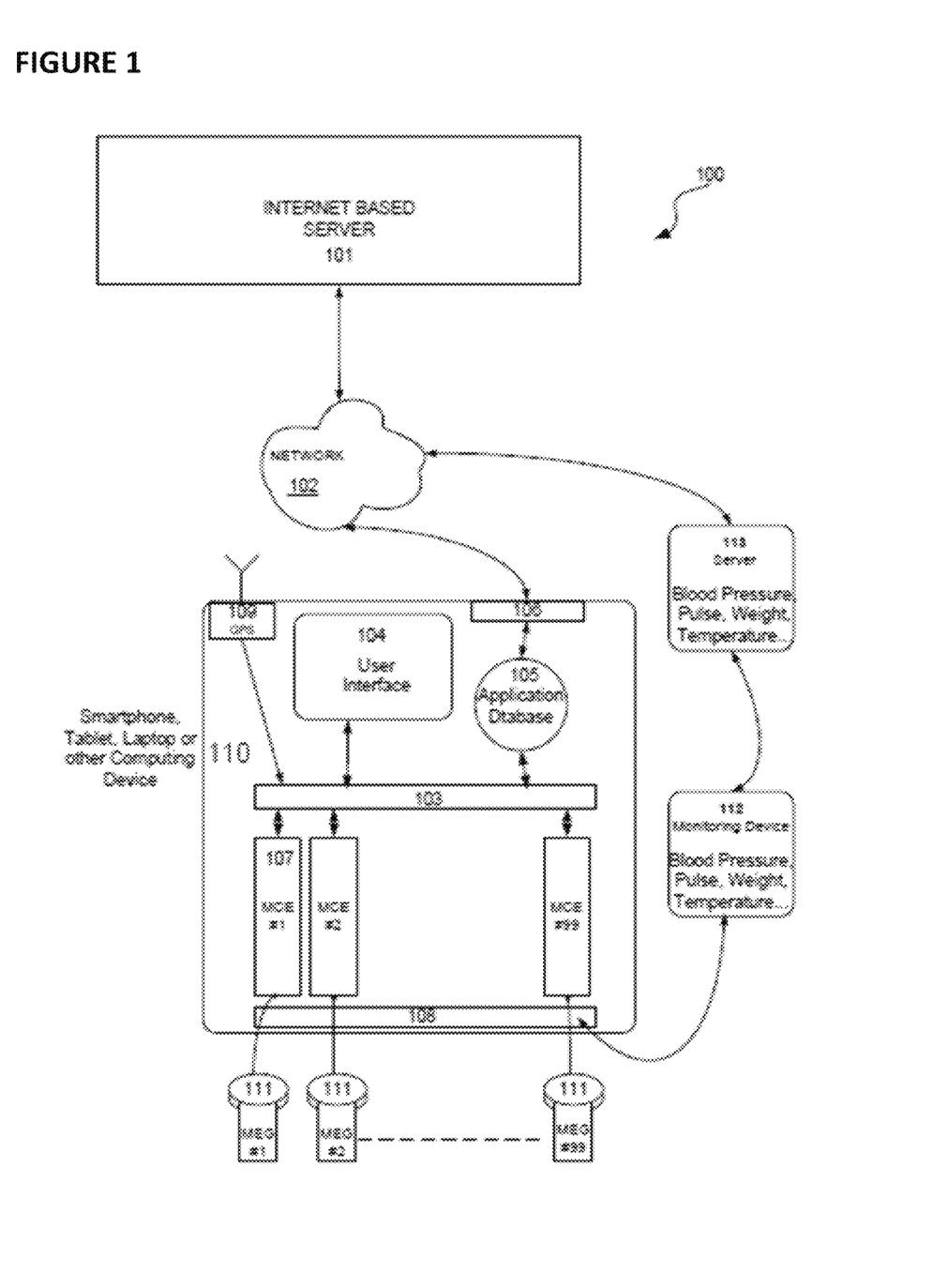
FIG. 1 is a schematic block diagram in accordance with one embodiment of the present invention.

FIG. 1 depicts a schematic block diagram of an exemplary system 100 including a network 102 (which can be a LAN, WAN, the internet, etc.) coupled to a computing device 110 (such as a smartphone, tablet, laptop or other such electronic device). Internet based server 101 is also suitably coupled to one or more computing devices 110 through network 102. Computing devices 110 can be any device with a browser or any smartphone or tablet with apps (applications).

Computing devices 110 are suitably coupled to one or more smart dispensers 111 through a built in southbound interface 108 or an external adapter. As used herein, the term "smart dispensers" refers to medication containers capable of generating events. These events can indicate, for example, the opening or closing of the smart dispenser, the change in weight of the contents of the smart dispenser, and/or other changes in the smart dispenser or its contents.

Figure 4:
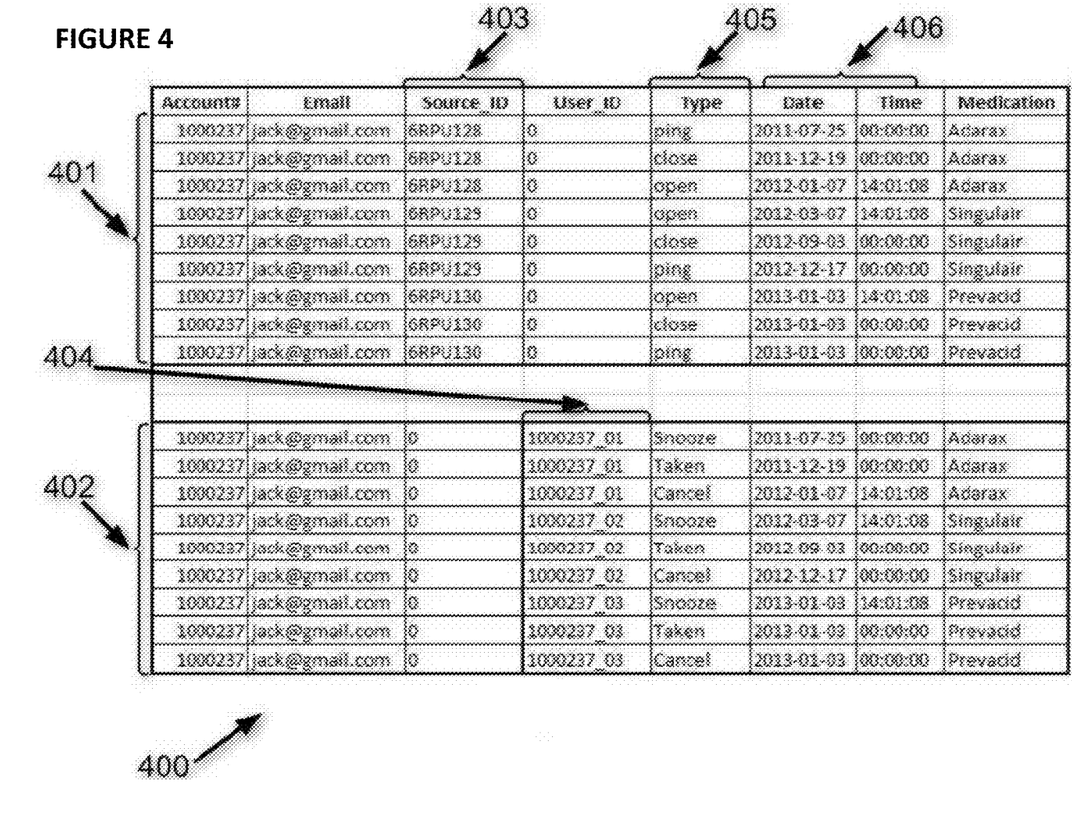
FIG. 4 depicts exemplary fields within a sample database in an internet based server that show events attributed to a patient's medication in one embodiment of the present invention. This figure shows events from the patient's smart dispensers and the patient's smartphone or other computing devices.

As used herein, unless expressly stated otherwise, "events" means signals and/or messages that are generated by the structures and devices described herein. These events are stored in the cloud server's database as shown in FIG. 4. Insights derived from any meaningful correlation of such events with any other data available on the cloud server's database can in turn generate derivative and recursive events. For example, deviation from normal times of medication consumption, overdosing on one while skipping another medication, projected refill ordering dates for medications, projected expiration dates for medications or any other valuable information derived regarding any medications in use by the patient.

Southbound Interface 108 communicates with the smart dispensers 111 using one or more wireless protocols, such as RF; IrDA (infrared); Bluetooth; ZigBee (and other variants of the IEEE 802.15 protocol); IEEE 802.11 (any variation); and ultrasound interfaces and specifications.

Network Interface 106 allows the computing devices 110 to communicate with Internet based server 101 through network 102. Network Interface 106 communicates using wireless or wired protocols, such as Cellular, 3G, 4G, LTE, RF; IrDA (infrared); Bluetooth; ZigBee (and other variants of the IEEE 802.15 protocol); IEEE 802.11 (any variation); ultrasound interfaces and specifications; or Ethernet.

Internet based server 101 in the illustrated embodiment can be implemented as a cloud based server using both public, private and hybrid cloud configurations. The cloud server contains all the configuration and monitoring data in a centralized database and communicates with the patients, multiple caregivers, smart dispensers 111 and patient's computing devices 110 and monitoring devices 112 to help share, enhance and correlate the data in its database. Internet based server 101 in the illustrated embodiment implements all the security and data privacy safeguards to protect the patients' medical records for both data in transit and data at rest. This server is compliant with the requirements of industry specific security standards and regulations such as HIPAA and PCI.

Internet based server 101 in the illustrated embodiment allows the patient or caregivers to securely configure and monitor all the medications and enable their compliance monitoring with smart dispensers 111 and patient's computing devices 110.

Internet based server 101 in the illustrated embodiment also allows the patients to configure any monitoring devices 112 they are using such as blood pressure, temperature, pulse and weight monitors so these parameters can also be securely monitored by multiple caregivers providing a holistic view of the patient's health not just their medication compliance.

Internet based server 101 collects all the events and messages from each smart dispenser 111 of medication events and builds a database as shown in FIG. 4. This allows monitoring, tracking, trending and also provides in-depth analytics on the medications compliance by patients.

Internet based server 101 collects all the events and messages from each computing device 110 representing the patient's actions for each medication alert and builds a database as shown in FIG. 4. This allows monitoring, tracking, trending and also provides in-depth analytics on the patients compliance to the medication alerts.

Internet based server 101 correlates the events and messages from each smart dispenser 111 and the corresponding alerts and actions by the patient as seen from events and messages from device 110. A composite view of these two sources and events is shown in FIG. 4. FIG. 4 depicts exemplary fields from a database utilized by Internet based server 101 to adapt the logic for medication alerts, escalate so care givers intervene, create more actionable alerts based on patient's geo-location, and adjust alerting mechanisms to compensate for patient fatigue and the like.

Internet based server 101 is accessible through one or more computing devices 110 with a browser or one of more smartphones or tablets with an App. This provides patients or multiple caregivers access to monitoring, tracking, trending and also provides in-depth analytics on the usage of medications by individual patients.

Internet based server 101 is used by patients or caregivers with computing devices 110 with a browser or one of more smartphones or tablets with an App (application), to create an account and to register each smart dispenser 111 to be used for each of the patient's medications. The patient or caregiver also specifies the details of the medication corresponding to each smart dispenser 111 such as schedules and dosages.

Internet based server 101 correlates multiple smart dispensers 111 registered to each patient and produces the corresponding monitoring, tracking, trending and provides in-depth analytics on the usage of multiple medications by individual patients.

Internet based server 101 in the illustrated embodiment communicates with Application Database 105 through the network interface 106. Application database 105 contains all the configuration data, status and events and constantly synchronizes this data with the cloud database.

Computing device 110 in the illustrated embodiment can be any smartphone or tablet with an App (application) or any device that contains or supports a browser and can access the Internet based server 101 over the internet. This includes all laptops, desktops, tablets and smartphones and other internet enabled electronic devices like gaming consoles and televisions etc.

A patient may also have one or more computing devices 110. Such devices should be able to receive events and messages from smart dispensers 111, as well as monitoring devices 112 that measure a patients pulse, blood pressure, temperature, weight and the like. The computing devices 110 can process and present these events and messages, in whatever form, to the patient and also forward these to the internet based server 101 for review by multiple caregivers and also for tracking, trending and analytics.

Medication Compliance Enforcer (MCE) 107 in the illustrated embodiment communicates with Application Backplane 103 to transmit and receive events, status and configuration data to and from the cloud database. Each MCE 107 comprises lines of software code and associated data structures executed and utilized by computing device 110.

Figure 7:
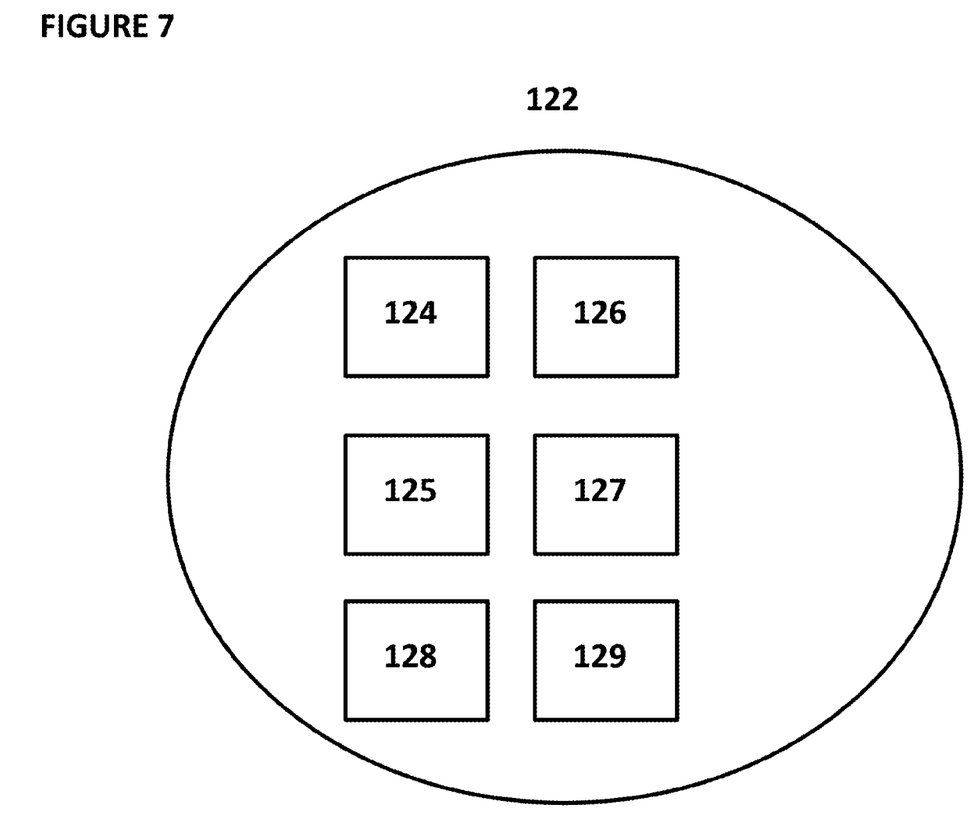
FIG. 7 depicts components of circuitry within a smart dispenser.

Global Positioning System (GPS) 109 in the illustrated embodiment can be implemented with the built-in GPS functionality of a smartphone or tablet or any computing device 110, it can also be implemented with an external GPS receiver. The information for individual smart dispensers 111 can be obtained from their GPS unit 129 which provides GPS location information for the smart dispenser 111. Alternatively the GPS location of smart dispenser 111 can be determined from the patient's location which is determined by the GPS location of his computing device 110 and by correlating this information with the range of the data communication method used.

GPS 109 communicates with the Application Backplane 103 to provide GPS coordinates that can be used by the MCEs 107, User Interface 104 and Application Database 105 to qualify all events and messages with the current geo location of the patient and smart dispensers 111.

Application backplane 103 in the illustrated embodiment is a clearing house of information. It communicates with application database 105, GPS interface 109, User Interface 104 and each MCE 107 to enable configuration of individual MCEs from the cloud, collect events and status from each MCE and update both the cloud and the user interface. Application backplane 103 also collects GPS coordinates from GPS interface 109 allowing the MCEs, the cloud and the user interface to correlate the geo location of both the patient and the smart dispensers 111 with the events and patient's responses.

Application database 105 in the illustrated embodiment locally stores a copy of the information held in the internet based server 101 about the patient's medications, medication schedule times, dosages etc. It communicates with application backplane 103 and exchanges information with the MCEs 107, user interface 104, GPS interface 109 and the internet based server 101 through the network interface 106.

Application database 105 is constantly updated with data from the internet based server 101, the events from all smart dispensers 111 and MCEs 107. The user interface 104 and GPS 109 also communicate with and modify the application database 105 which serves as the main source of information that drives the complex logic for issuing, canceling, and timing alerts to the patient through the user interface 104 and using audio, visual and multi-media, email and SMS cues and alerts.

GPS 109 enables the MCEs 107, user Interface 104 and application database 105 to utilize the GPS coordinates and identify the location of each smart dispenser 111, this is done by determining the patient's location and correlating the range of the data communication protocols, techniques, or methodologies, including, without limitation: RF; IrDA (infrared); Bluetooth; ZigBee (and other variants of the IEEE 802.15 protocol); IEEE 802.11 (any variation); and ultrasound interfaces.

GPS 109 enables the MCEs 107, User Interface 104 and Application Database 105 to correlate the location of the patient and each of the smart dispensers 111, this allows for more actionable alerts such as but not limited to pre pone and post pone alerts to make sure the patient is within range of the smart dispenser 111. The use of location also allows the internet based server 101 to isolate communication problems related to power, broadband, DSL, cable etc. to a particular location and help isolate and correct the problems so that communication with smart dispensers 111 is restored.

GPS 109 allows the MCEs 107, User Interface 104 and Application Database 105 to provide the interest based server 101 with location of the patient and each of the smart dispensers 111 for each event and message. This allows the internet based server 101 to determine the location of the smart dispensers 111, the patient's location at the predefined medication schedule times and determine why medication schedules aren't being met and make appropriate changes to the enforcement logic and improve compliance. One such change in enforcement logic alerts the patient of impending medication schedule times as the patient moves away from the location of the smart dispensers 111. Another such change in enforcement logic alerts the patient of impending or missed medication schedule times as the patient approaches the location of the smart dispensers 111.

Internet based server 101 tracks the location of smart dispensers 111 based on their last known location as reported by the MCEs 107 and application database 105 based on GPS coordinates from GPS 109. This information among other uses is also used to alert the multiple caregivers if the smart dispenser is displaced from its normal location.

Figure 3:
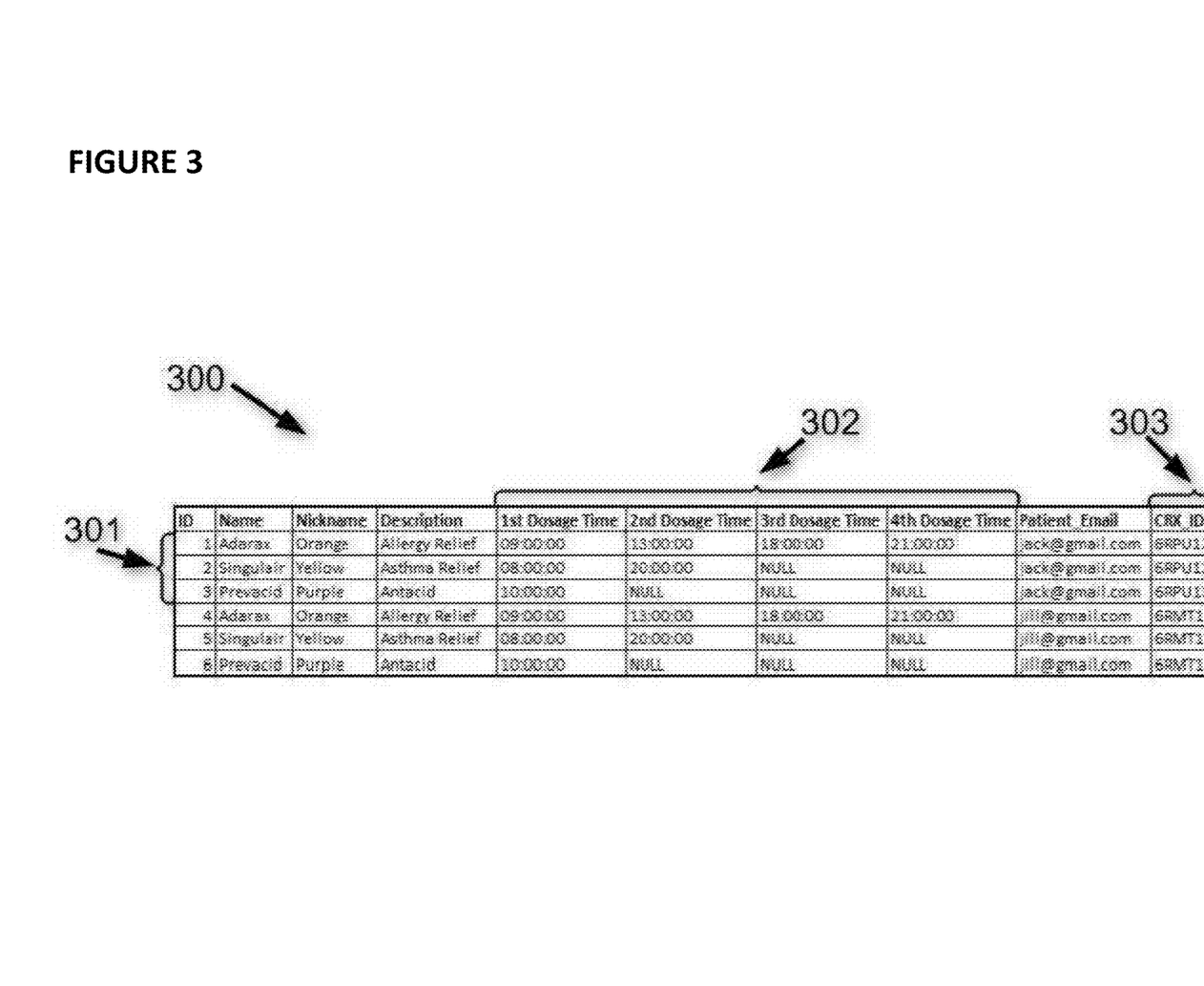
FIG. 3 depicts exemplary fields within a sample database in an internet based server that show medications and schedules for patients in one embodiment of the present invention.

Each MCE 107 in the illustrated embodiment is configured with the data in the internet based server 101 for a specific patient's specific medication. Thus a patient who takes three medications as shown in FIG. 3 will have three MCEs 107 configured with all the medication and scheduling data for that patient from the internet server 101.

Each MCE 107 in the illustrated embodiment is configured with the data from the internet based server 101 for the patient's medication. The patient is not required to enter any data locally. This allows a caregiver or a concierge service to create and review this data reliably and also allows for this data to be imported from reliable sources like a database from the pharmacy that supplied the medication to the patient.

Figure 2:
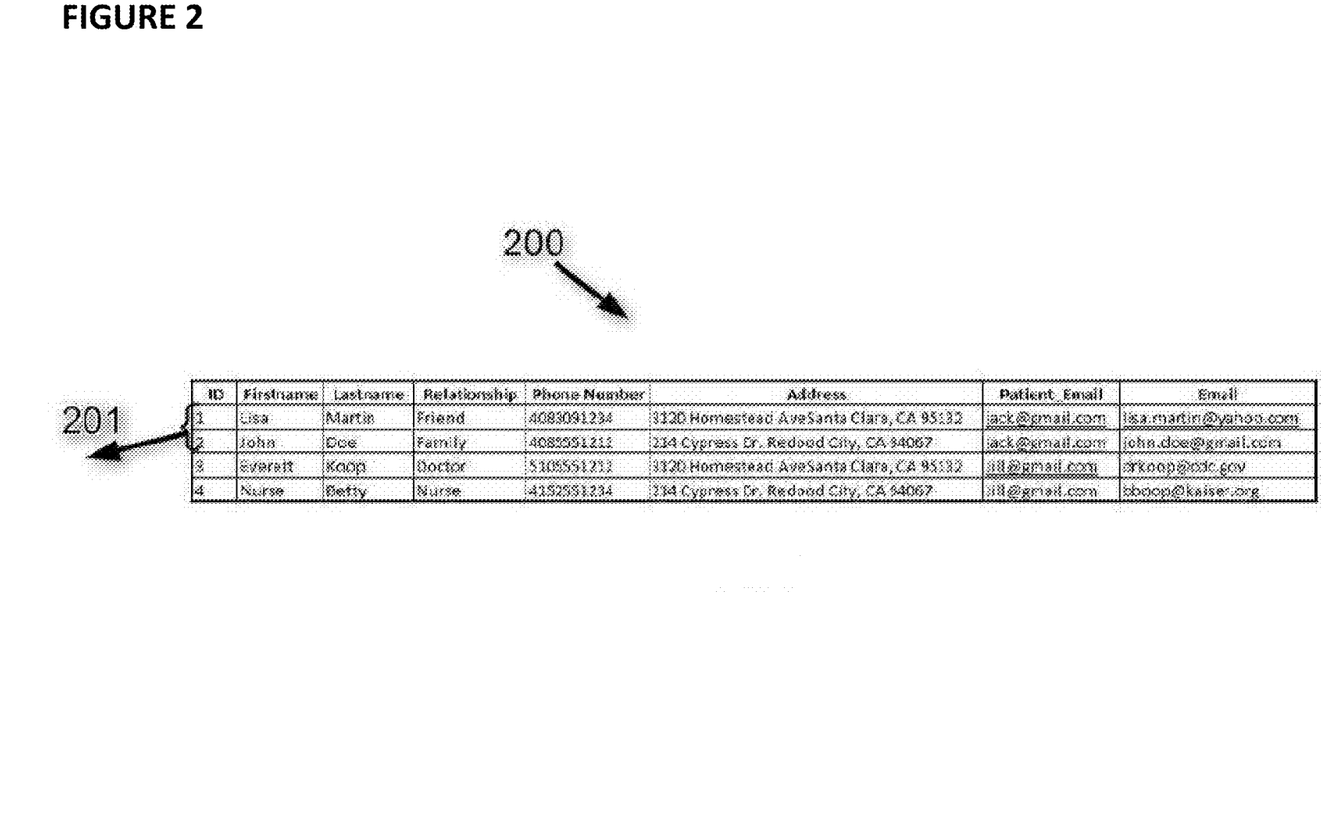
FIG. 2 depicts exemplary fields within a sample database in an internet based server that show patients and their corresponding caregivers in one embodiment of the present invention.

Each MCE 107 in the illustrated embodiment is configured to receive events from a smart dispenser 111 these events are also sent to the internet based server 101. This allows both the patient with computing devices 110 locally and multiple caregivers as shown in FIG. 2. from the cloud to access the data and monitor the patient's compliance.

Each MCE 107 in the illustrated embodiment communicates with a smart dispenser 111 through Southbound Interface 108. Each smart dispenser 111 is assigned to a unique MCE 107.

MCE 107 reacts to each event from a smart dispenser 111 and correlates it with the information in application database 105 for the medication schedule corresponding to that smart dispenser 111 and also evaluates the patient's location from GPS 109 and patients responses from user interface 104. This analysis allows the MCE 107 to postpone, cancel pending alerts, generate new alerts or combine impending alerts with pending alerts while ensuring the alerts are actionable based on the patient's location relative to his medications and also reinforcing compliance with escalation of events based on numerous and/or critical pending medications schedules by using audio, video, multimedia cues and also email and SMS alerts as well as alerting caregivers.

Southbound Interface 108 receives messages and events from each smart dispenser 111 and processes and directs them to the MCE 107 assigned to that smart dispenser 111.

A Monitoring device 112 communicate with computing devices 110 over the Southbound Interface 108 using wireless data communication protocols, techniques, or methodologies, including, without limitation: RF; IrDA (infrared); Bluetooth; ZigBee (and other variants of the IEEE 802.15 protocol); IEEE 802.11 (any variation); and ultrasound interfaces.

A Monitoring device 112 may also communicate with computing devices 110 over an industry standard or mutually agreed upon API using wireless data communication protocols, techniques, or methodologies, including data exchange through an interface with the local or network based server for the monitoring device 113.

Figure 5:
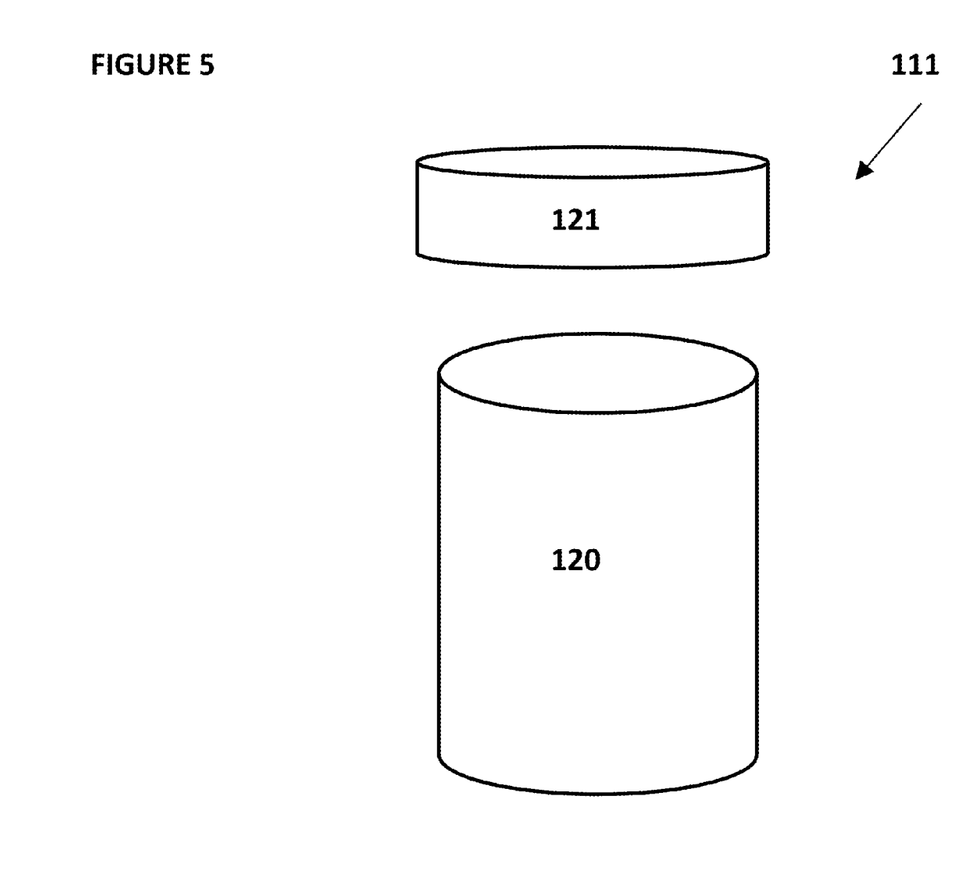
FIG. 5 depicts an embodiment of a smart dispenser.
Figure 6:
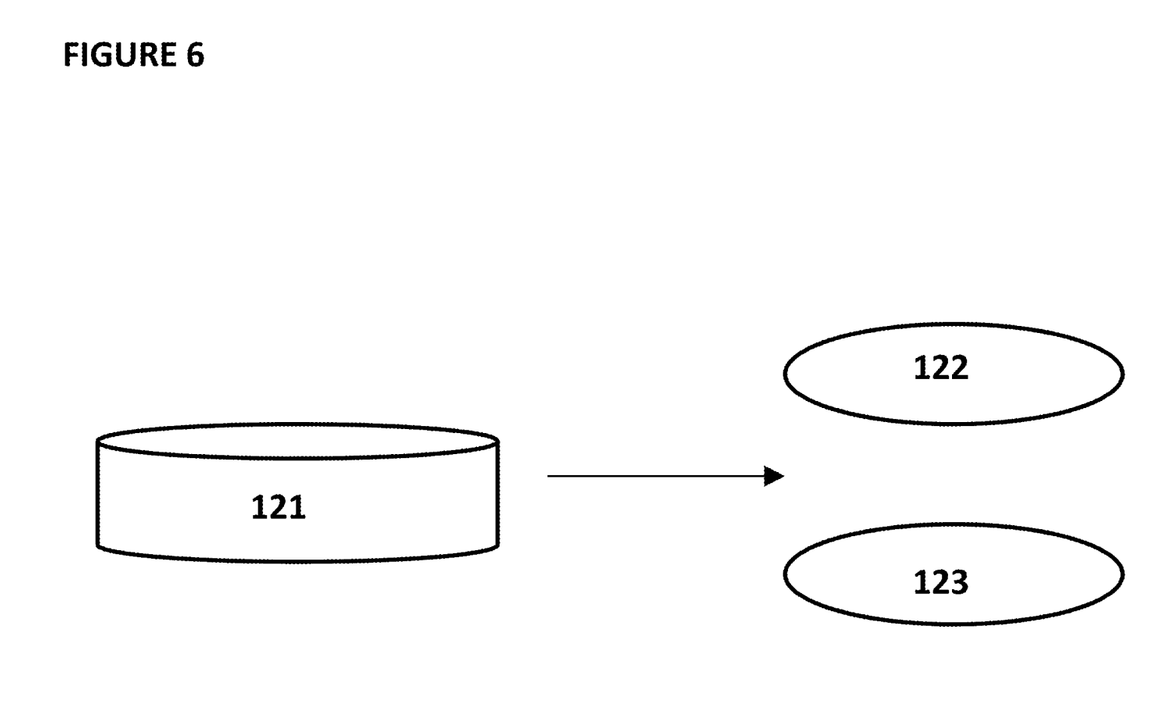
FIG. 6 depicts an embodiment of components of a smart dispenser.

Additional detail regarding an embodiment of smart dispenser 111 is shown in FIGS. 5-7. As shown in FIG. 5, smart dispenser 111 can comprise container 120 and cap 121. The exterior structures of container 120 and cap 121 optionally can resemble a traditional pill bottle constructed of plastic. During operation, container 120 will hold medication.

With reference to FIG. 6, cap 121 comprises circuitry 122 and battery 123. Battery 123 provides power for circuitry 122 and optionally can be a rechargeable battery.

With reference to FIG. 7, an embodiment of circuitry 122 is depicted. Circuitry 122 optionally can comprise a printed circuit board (PCB) and/or an integrated circuit chip. In this embodiment, circuitry 122 comprises controller 124, non-volatile memory 125, memory 126, wireless interface 127, sensor 128, and GPS unit 129. Optionally, sensor 128 could instead be located on container 120, or sensor 128 would be contained partially on cap 121 and partially on container 120.

Non-volatile memory 125 stores firmware utilized by smart dispenser 111. Memory 126 is used to store data corresponding to events during operation of smart dispenser 111. GPS unit 129 provides GPS location information for smart dispenser 111.

Sensor 128 is configured to detect the opening and/or closing of smart dispenser 111. For example, sensor 128 can be comprise a first piece on cap 121 and a second piece on container 120, where a magnetic coupling is formed between the first piece and second piece when cap 121 is secured on container 122 and the magnetic coupling is broken when cap 121 is removed from container 122. The breaking of the magnetic coupling can result in sensor 128 sending an electrical signal representing an event to controller 124. In the alternative, sensor 128 instead may be a pressure sensor, a piezoelectric sensor, a light sensor, a motion sensor or the like. If more than one sensor is used, the sensors need not all be of the same kind. The function of sensor 128 in this set of embodiments is to detect that smart dispenser 111 has been opened and closed. Any sensor (alone or in combination with one or more other sensors) that achieve this function is acceptable. In these embodiments, system 100 assumes that if the smart dispenser 111 containing medications has been opened and then closed, that the medication was actually taken and that the dosage was correct.

In another embodiment, circuitry 122 instead can be located in the bottom of container 120, and sensor 128 can be a weight detector that will send an electrical signal to controller 124 when the detected weight changes, as would be the case when a pill is removed. The signal optionally can indicate the amount by which the weight changed. Controller 124, computing device 110, and/or internet based server 101 can be configured with weight information for the pills in container 120, and in this situation, the data collected by sensor 128 can be used to determine how many pills have been added to or removed from smart dispenser 111.

Smart dispenser 111 in the illustrated embodiment communicates with southbound interface 108 using wireless interface 127. Wireless interface 127 implements one or more wireless data communication protocols, techniques, or methodologies, including, without limitation: RF; IrDA (infrared); Bluetooth; ZigBee (and other variants of the IEEE 802.15 protocol); IEEE 802.11 (any variation); and ultrasound interfaces.

Smart dispenser 111 generates suitable events and messages over wireless interface 127. These events and messages indicate the opening, closing etc. of the smart dispenser's cap (or lid) and the displacement, weight, etc. of the smart dispenser.

Each smart dispenser 111 periodically communicates with the internet based server 101 to establish that the communication link is functional; this assures that the power, broadband, DSL, Cable and all other circuitry are functional and serves as a troubleshooting aid.

Each smart dispenser 111 is powered by battery 123 and stores all events in memory 126 for up to a few months and transmits them when reliable power and communications are restored. This allows the patient to travel with the smart dispensers 111 both on day trips and extended stays without any power or internet connectivity and still be able to monitor his medication adherence. Smart dispenser 111 optionally can retransmit events to internet based server 101 to ensure that any communication failures at the patient's location, the internet or the internet based server 101 do not cause any events and status information to be lost.

Internet based server 101 supports retransmission of duplicate events by smart dispensers 111 and reconciles them in its centralized database to ensure that any communication failures at the patient's location, the internet or the internet based server 101 do not cause any events and status information to be lost.

FIG. 2 illustrates exemplary fields 200 within a sample database in the internet based server 101. The exemplary fields 200 show two records or rows 201 corresponding to the patient's caregivers and their detailed information. The exemplary fields 200 also show records for another patient and groups each patient's caregivers based on the patient's email address in one embodiment of the present invention.

FIG. 3 illustrates exemplary fields 300 within a sample database in the internet based server 101. The exemplary fields 300 shows three records or rows 301 corresponding to a patient's medications and their detailed information. The exemplary fields 300 also shows records for another patient and groups each patient's medications based on the patient's email address in one embodiment of the present invention. The exemplary fields 300 also shows the medication schedules and dosages 302 for each of the patient's medications. In one embodiment of the present invention the exemplary fields 300 also shows the identifier 303 that uniquely identifies each medication assigned to each patient and associates events and messages that contain this identifier with the smart dispenser 111 used by the patient for the medication.

FIG. 4 illustrates exemplary fields 400 in a sample database 400 in the internet based server 101. The exemplary fields 400 shows several records or rows 401 corresponding to events and messages received from smart dispensers 111 in use by a patient. For rows 401, the exemplary fields 400 also show details of the events and messages such as source 403 which identifies the unique smart dispenser 111 that generated the event, the event type 405 such as opening, closing or network diagnostics, the data and time 406 the event was generated.

The exemplary fields 400 also shows several records or rows 402 corresponding to events and messages received from the patient's smartphone, tablet or other computing devices 110. For rows 402 the exemplary fields 400 also show details of the events and messages such as source 404 which identifies each unique medication the patient is using, the response type 405 such as cancel, snooze, taken or skipped medication, the data and time 406 the event was generated.

In one embodiment of the present invention the exemplary fields 400 for both the rows 401 and 402 also includes the location of the patient and smart dispensers 111 from each event and message received.

Figure 8:
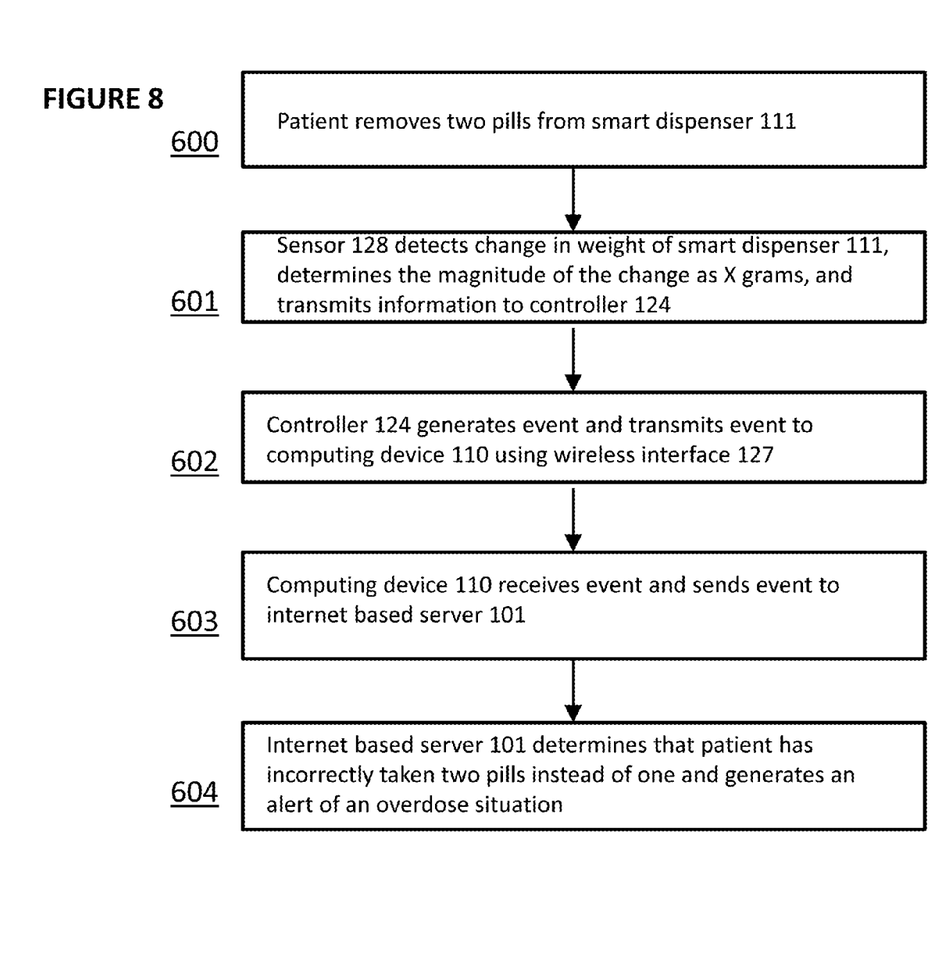
FIG. 8 depicts an exemplary method of identifying a medication overdosage by a patient.
Figure 9:
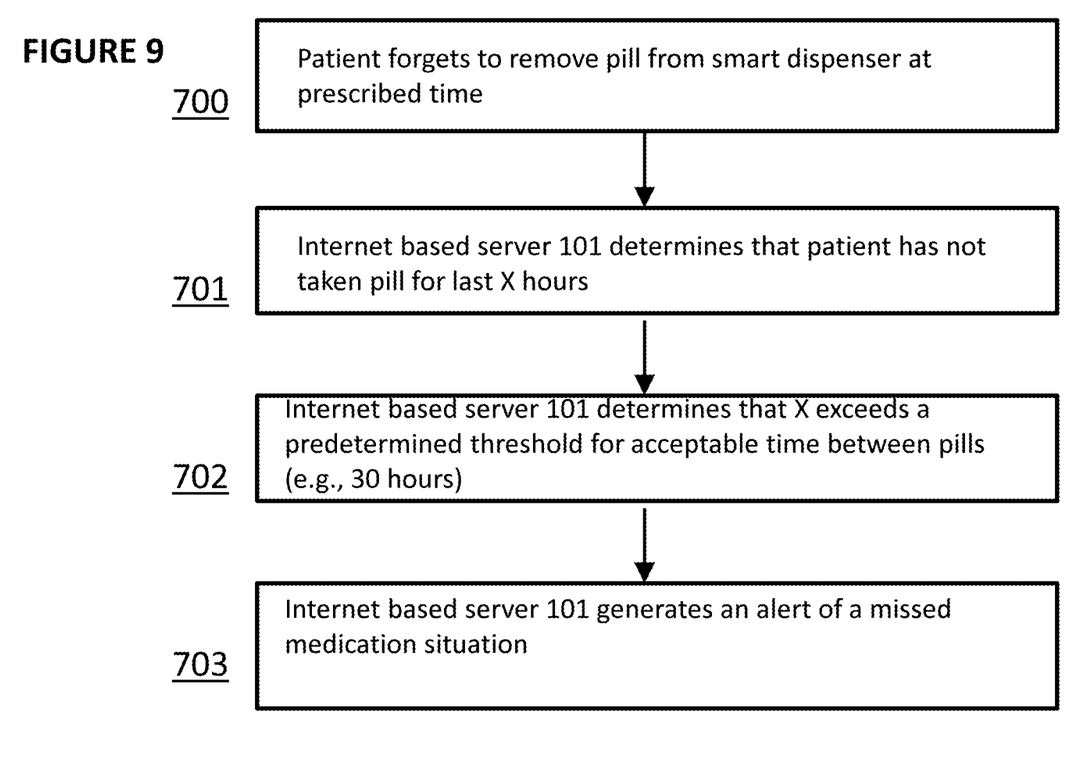
FIG. 9 depicts an exemplary method of identifying a missed medication event by a patient.

The utility of the systems and methods described thus far will now be illustrated in FIGS. 8 and 9. With reference to FIG. 8, a patient removes two pills from smart dispenser 111 (step 600). Sensor 128 detects the change in weight of smart dispenser 111, determines the magnitude of the change as X grams, and transmits the information to controller 124 (step 601). Controller 124 generates an event and transmits the event to computing device 110 using wireless interface 127

(step 602). Computing device 110 receives the event and sends the event to internet based server 101 (step 603). Internet based server 101 determines that patient has incorrectly taken two pills instead of one and generates an alert of an overdose situation (step 604). In this embodiment, Internet based server 101 has stored the weight of each pill in its database and has associated that pill with the patient and smart dispenser 111 (such as by creating a record comprising the patient's ID, the ID for smart dispenser 111, and the weight information for the pill used in smart dispenser 111). The alert can take many different forms, such as an email, SMS, MMS, phone call, or voice message sent to the patient, a caregiver, a 911 dispatcher, or another person.

With reference to FIG. 9, a patient forgets to remove a pill from smart dispenser at the prescribed time (step 700). Internet based server 101 determines that patient has not taken pill for last X hours (step 701). This would occur, for instance, if sensor 128 does not detect an opening and closing of smart dispenser 111 during the last X hours. Internet based server 101 determines that X exceeds a predetermined threshold for acceptable time between pills (e.g., 30 hours) (step 702). Internet based server 101 generates an alert of a missed medication situation (step 703). The alert can take many different forms, such as an email, SMS, MMS, phone call, or voice message sent to the patient, a caregiver, a 911 dispatcher, or another person.

Thus, cloud based monitoring can ensure compliance with medication regimens and can prevent life threatening situations. Optionally, closed based monitoring using smart dispensers 111 can be deselected by a patient, a caregiver, or another involved person in which case the system solely depends on the self-reporting by the patient using the computing device 100.

Figure 10:
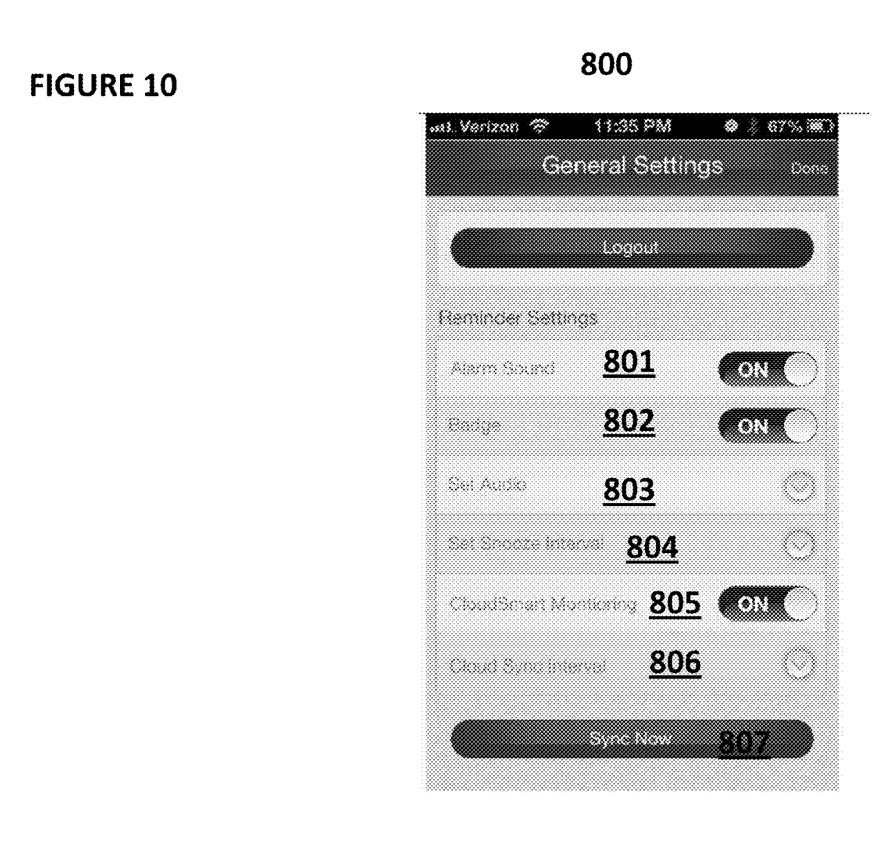
FIG. 10 depicts a screen shot of an exemplary user interface for a computing device used in conjunction with the embodiments of the present invention.

FIG. 10 depicts a screen shot of an exemplary user interface 800 for computing device 110. In this example, computing device 110 is a smartphone or tablet. User interface 800 comprises a plurality of input devices that can be used by a patient, caregiver, or another involved person to configure various settings for a particular patient. For example, input device 801 is used to determine if an audible alarm will be used when an alert is generated by computing device 110 and/or internet based server 101. Input device 802 is used to determine if a pop up notification will be used when a medication due alert is generated by computing device 110. Input device 803 is used to select the sound used for the audible alarm. Input device 804 is used to set a "snooze interval," which allows the recipient to snooze the alarm (as might be used to see if the patient will remember to take his or her medication over the next Y minutes after the prescribed time has passed).

Input device 805 is used to turn on or turn off the "Cloud-Smart Monitoring" feature, which is the monitoring and enforcement mechanism by the Internet based server 101 described previously. This feature is useful if a patient, has already taken a medication for the scheduled time and the Internet based server 101 receives this event from the smart pill dispenser 111. This allows the Internet based server to notify the patient's computing device 110 that the upcoming alert for this medication schedule can be cancelled. The real benefit of CloudSmart Monitoring to the patient is that if all medications are taken as scheduled the patient will never be annoyed by unwanted alerts from his computing device 110.

Input device 806 is used to set the time interval between synchronization actions between computing device 110 and Internet based server 101. In this embodiment, input devices 801, 802, 803, 804, 805, and 806 are created using well-known HTML or JAVA devices such as buttons, menus, text boxes, etc.

References to the present invention herein are not intended to limit the scope of any claim or claim term, but instead merely make reference to one or more features that may be covered by one or more of the claims. Materials and processes described above are exemplary only, and should not be deemed to limit the claims.

What is claimed is:

1. A system for monitoring usage of medication and adaptively enforcing compliance with a medication schedule comprising:
   a medication dispenser configured to generate an event indicating one or more of an opening of the dispenser, a closing of the dispenser, or a change in weight of contents of the dispenser;
   a computing device coupled to the medication dispenser over a wireless network and configured to receive the event from the medication dispenser;
   an Internet based server coupled to the computing device over a wired or wireless network and configured to receive the event from the computing device;
   wherein the Internet based server is configured to generate an alert if an event is not received during a predetermined time period;
   wherein the computing device is configured to generate in response to the alert another event indicating the consumption or cancellation of a medication;
   wherein the computing device comprises a global positioning system (GPS) unit to generate a GPS location of the computing device; and
   wherein the Internet based server correlates the GPS location of the computing device and a location of the medication dispenser to adapt one or more medication schedules to ensure close proximity of the computing device to the medication dispenser to allow medication consumption.

* * * * *